United States Patent [19]

Adair

[11] Patent Number: 5,336,231
[45] Date of Patent: Aug. 9, 1994

[54] PARALLEL CHANNEL FIXATION, REPAIR AND LIGATION SUTURE DEVICE

[76] Inventor: Edwin L. Adair, 317 Paragon Way, Castle Pines Village, Colo. 80104

[21] Appl. No.: 979,931

[22] Filed: Nov. 23, 1992

Related U.S. Application Data

[63] Continuation-in-part of Ser. No. 877,076, May 1, 1992.

[51] Int. Cl.⁵ .................................................. A61B 17/00
[52] U.S. Cl. ............................................. 606/148; 606/1; 606/139
[58] Field of Search ............... 606/139, 144, 147, 148, 606/151, 1

[56] References Cited

U.S. PATENT DOCUMENTS

| | | | |
|---|---|---|---|
| 3,476,114 | 11/1969 | Shannon et al. | |
| 3,877,434 | 4/1975 | Ferguson et al. | |
| 4,018,229 | 4/1977 | Komiya | |
| 4,487,489 | 12/1984 | Takamatsu | |
| 4,493,323 | 1/1985 | Albright et al. | 606/144 |
| 4,602,635 | 7/1986 | Mulhollan et al. | |
| 4,607,621 | 8/1986 | Wheeler | |
| 4,760,848 | 8/1988 | Hasson | 606/222 |
| 4,935,027 | 6/1990 | Yoon | 606/148 |
| 5,037,433 | 8/1991 | Wick et al. | 606/139 |
| 5,100,421 | 3/1992 | Christoudias | 606/147 |
| 5,129,912 | 7/1992 | Noda et al. | 606/139 |
| 5,211,650 | 5/1993 | Noda | 606/139 |
| 5,234,443 | 8/1993 | Phan et al. | 606/144 |

FOREIGN PATENT DOCUMENTS

| | | | |
|---|---|---|---|
| 2804070 | 4/1977 | Fed. Rep. of Germany | |
| 0403111 | 10/1909 | France | 606/139 |
| 0163715 | 7/1964 | U.S.S.R. | 606/139 |
| 552077 | 1/1978 | U.S.S.R. | |

*Primary Examiner*—Stephen C. Pellegrino
*Assistant Examiner*—Jeffrey A. Schmidt
*Attorney, Agent, or Firm*—Fields, Lewis, Pittenger, Rost & Smith

[57] ABSTRACT

A laparoscopic fixation, repair and ligation suture; and device has a central passageway with first and second parallel channels on opposite sides thereof. A suture extends through the central channel passageway and has a loop with a slip knot on the distal end and a pull on the proximal end. By pulling on the pull the loop can be drawn tightly about a tissue to be ligated. A nesting tube is provided in one channel to receive a suture needle attached to a loopless suture to easily suture to a body cavity wall. In another form, a tapered handle frictionally receives a suture needle attached to a looped and slip knotted suture to repair a tear or rupture in a body part by suturing through one or more laparoscopies without tying ligature knots inside the body cavity. In a third form, a curved carrying device in one channel and a ligation assist device in the other channel permits ligation of large vessels attached to a body part by fibrous tissue.

6 Claims, 7 Drawing Sheets

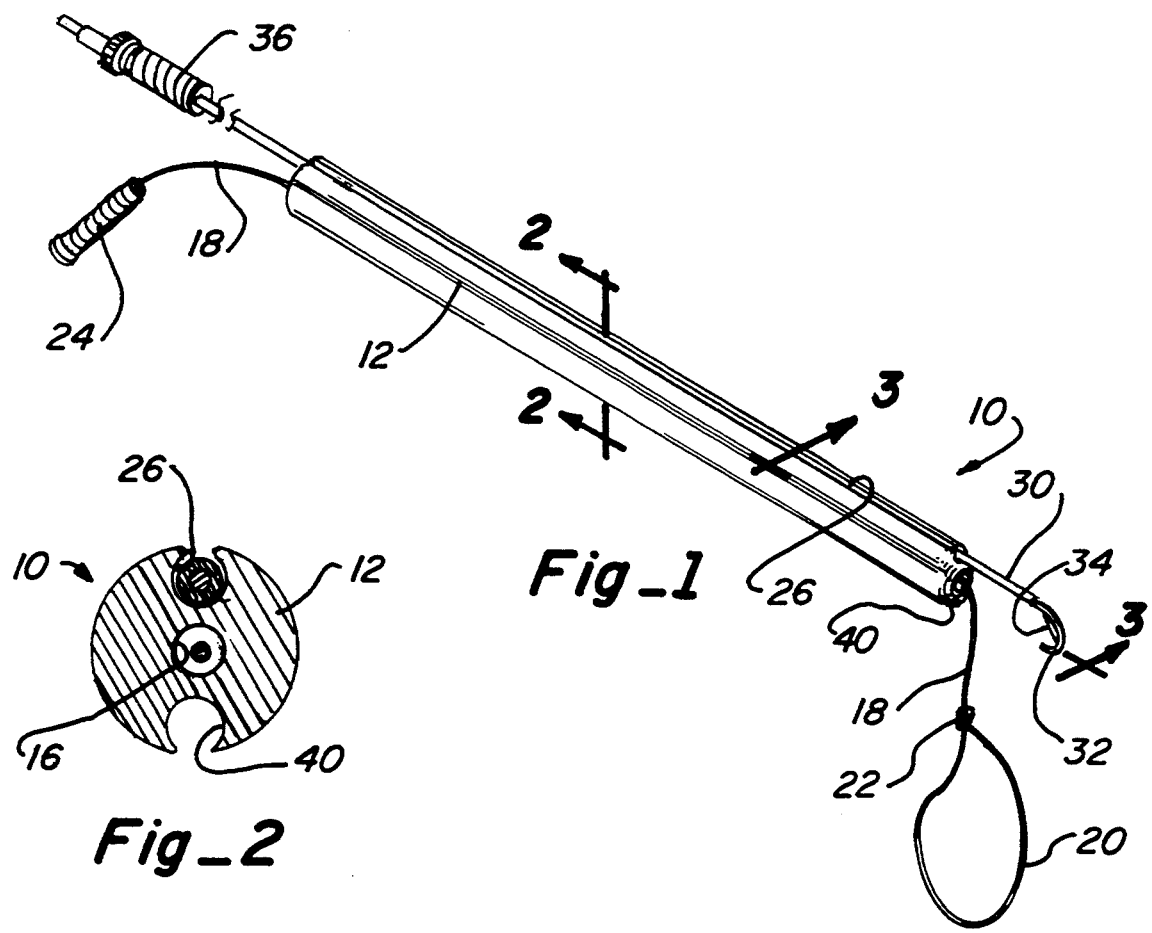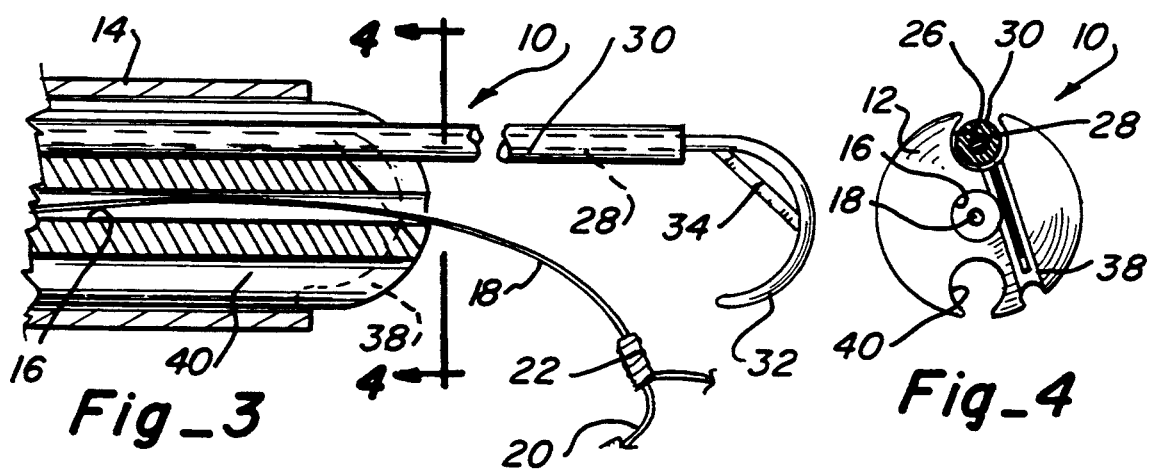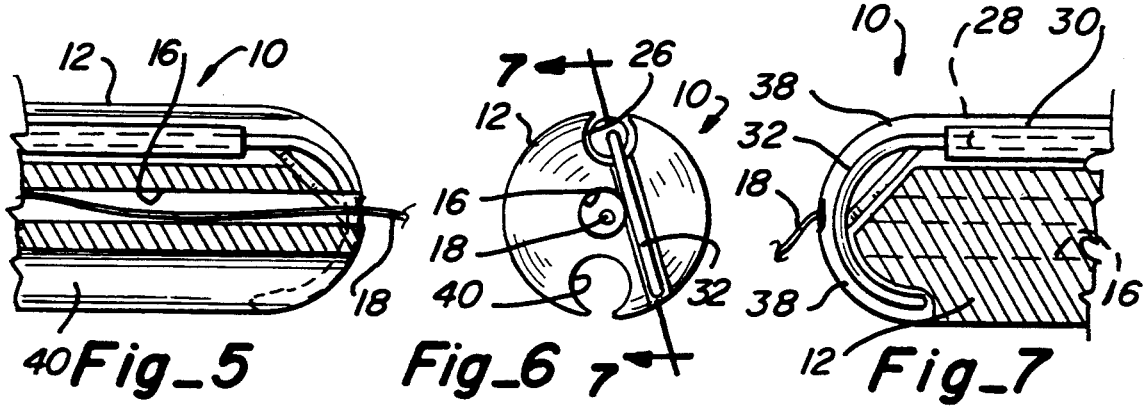

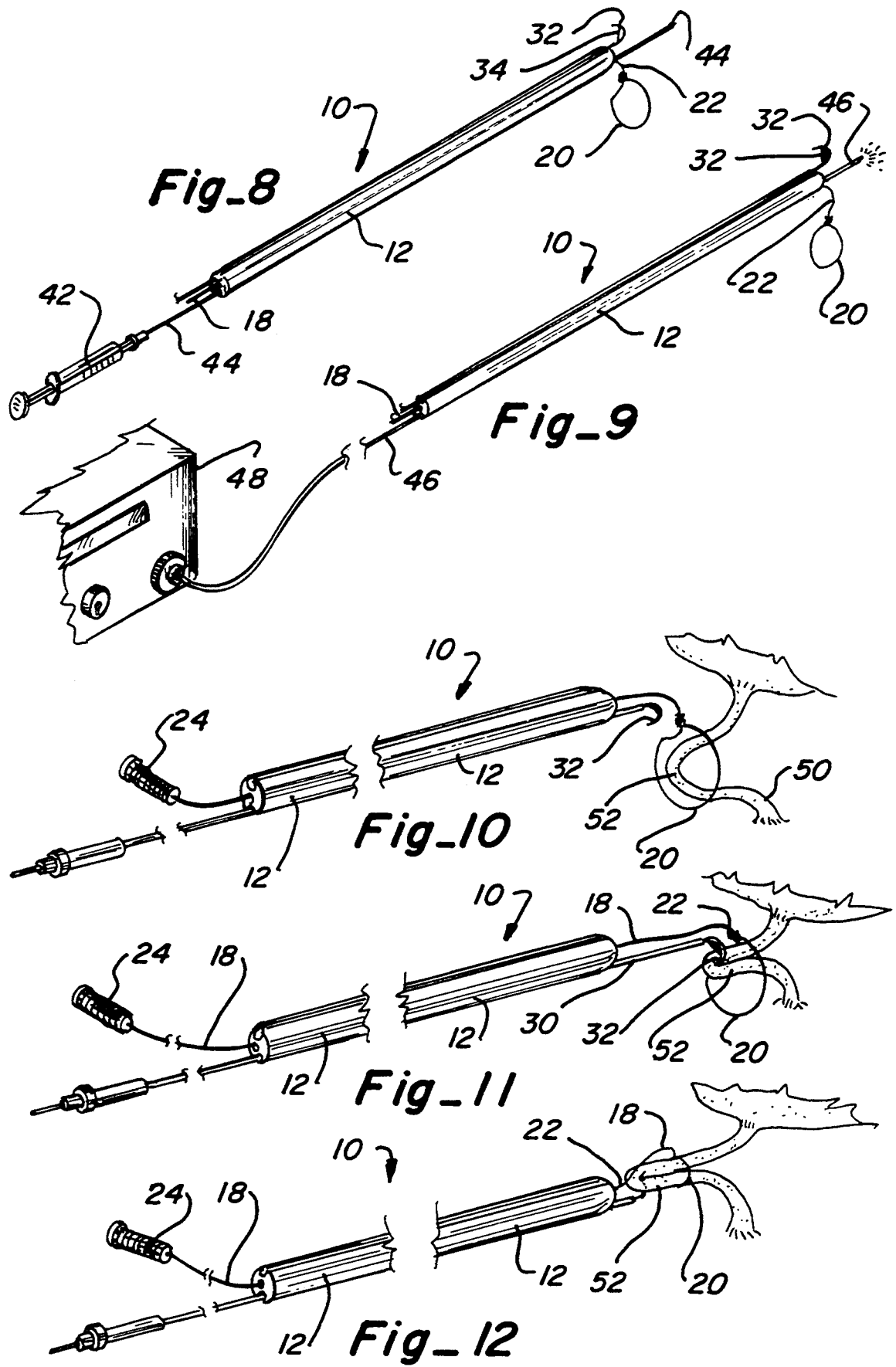

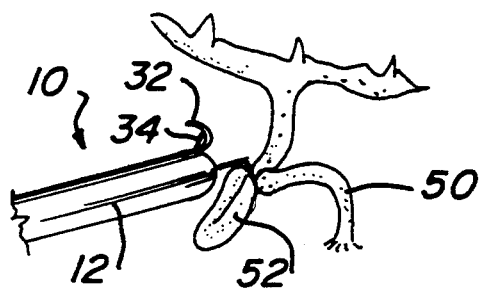
Fig_13
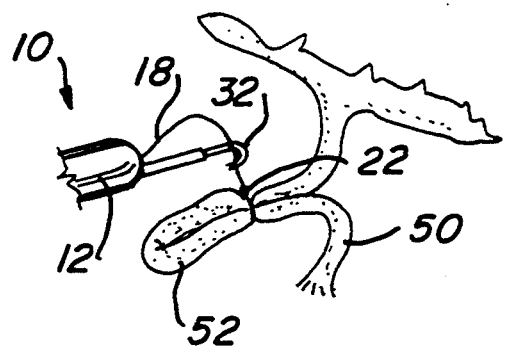
Fig_14
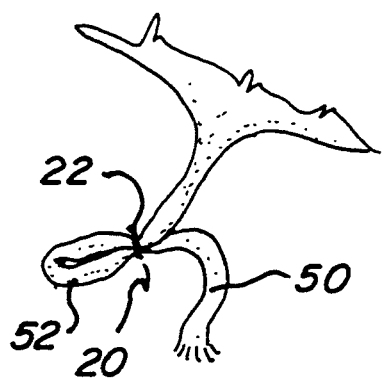
Fig_15
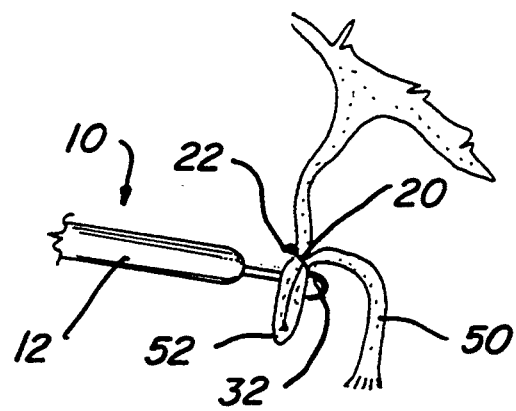
Fig_16
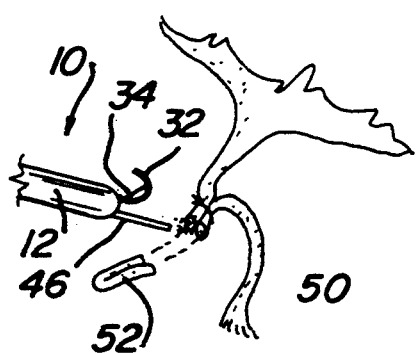
Fig_17

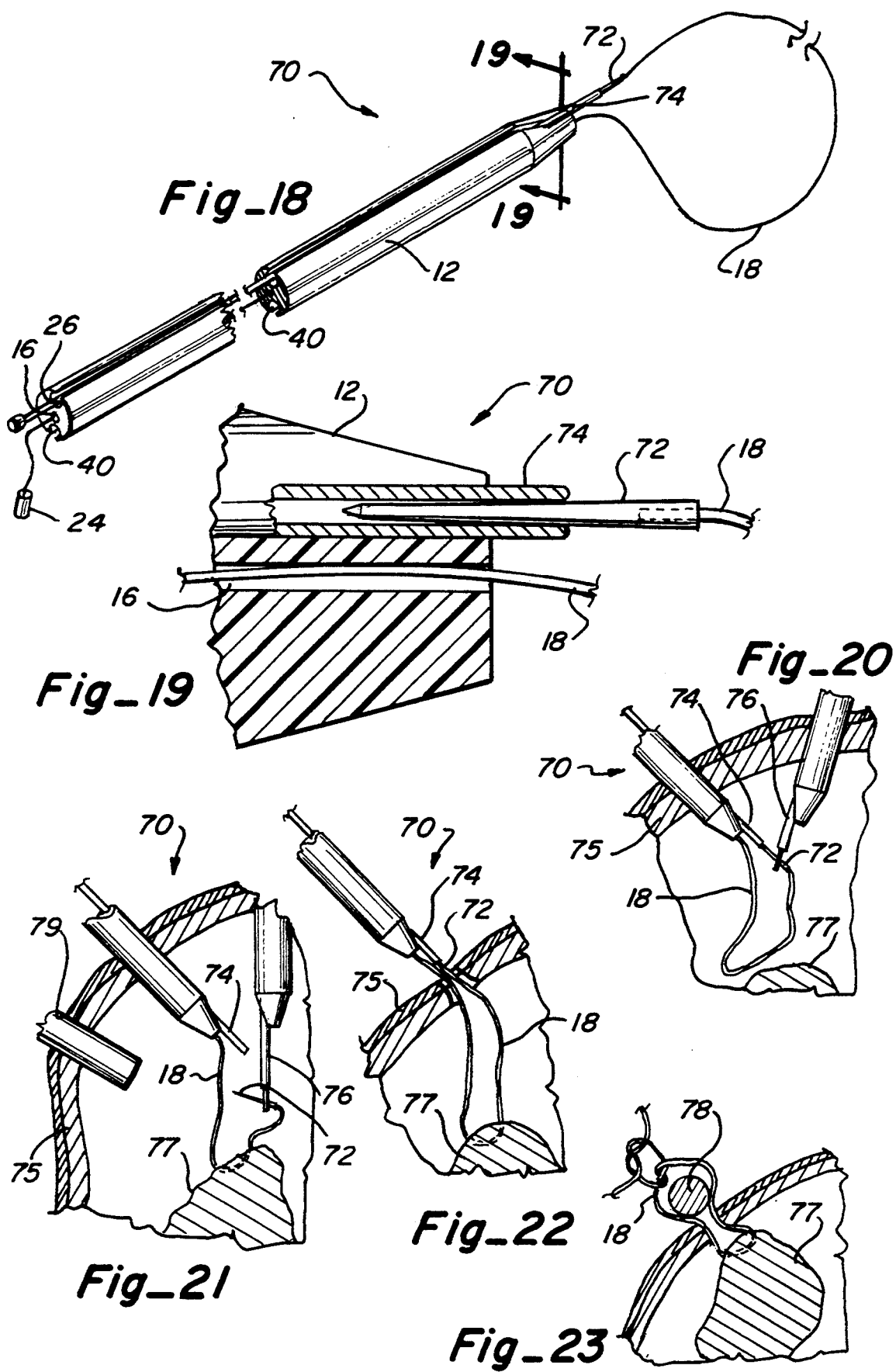

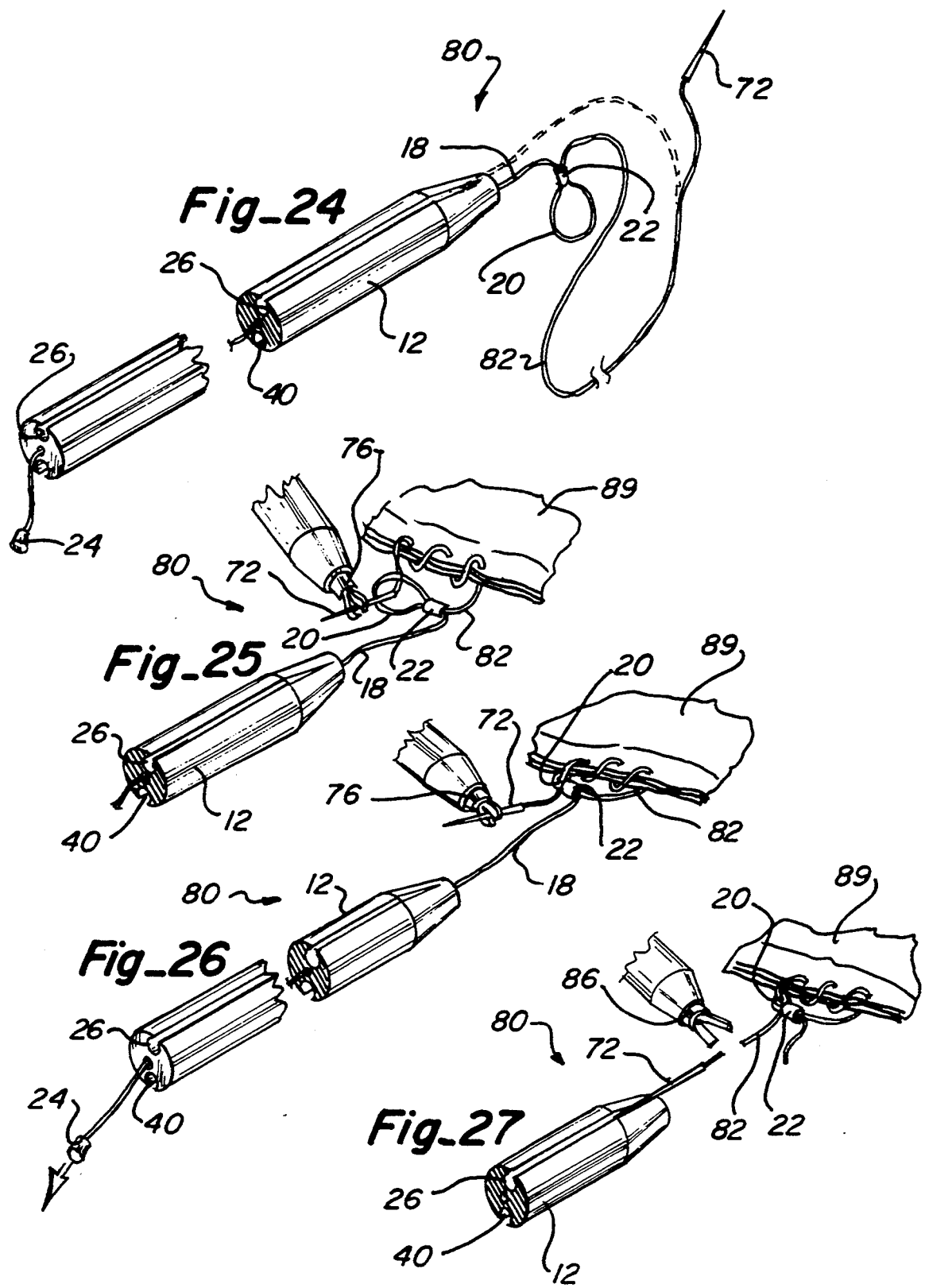

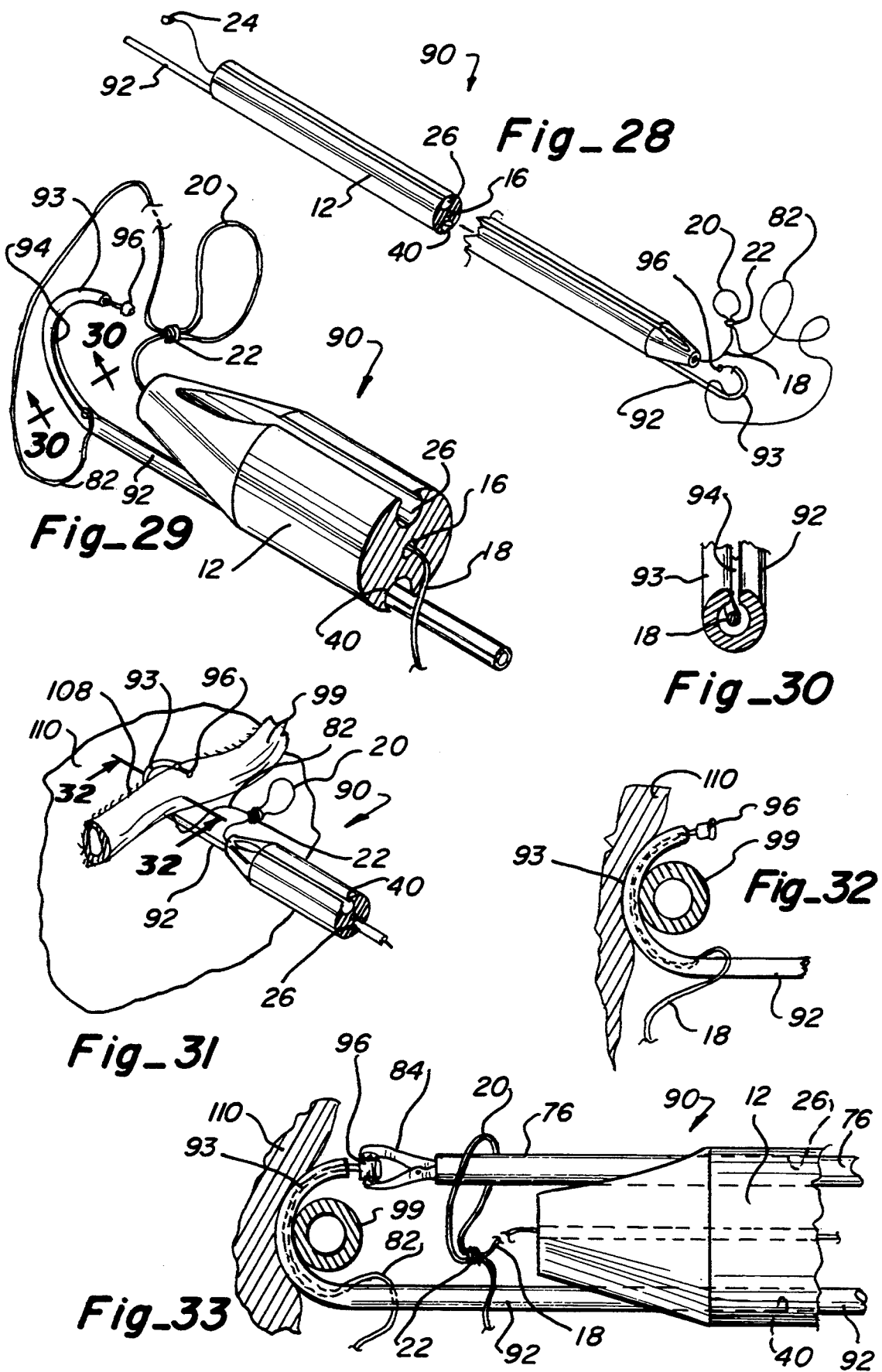

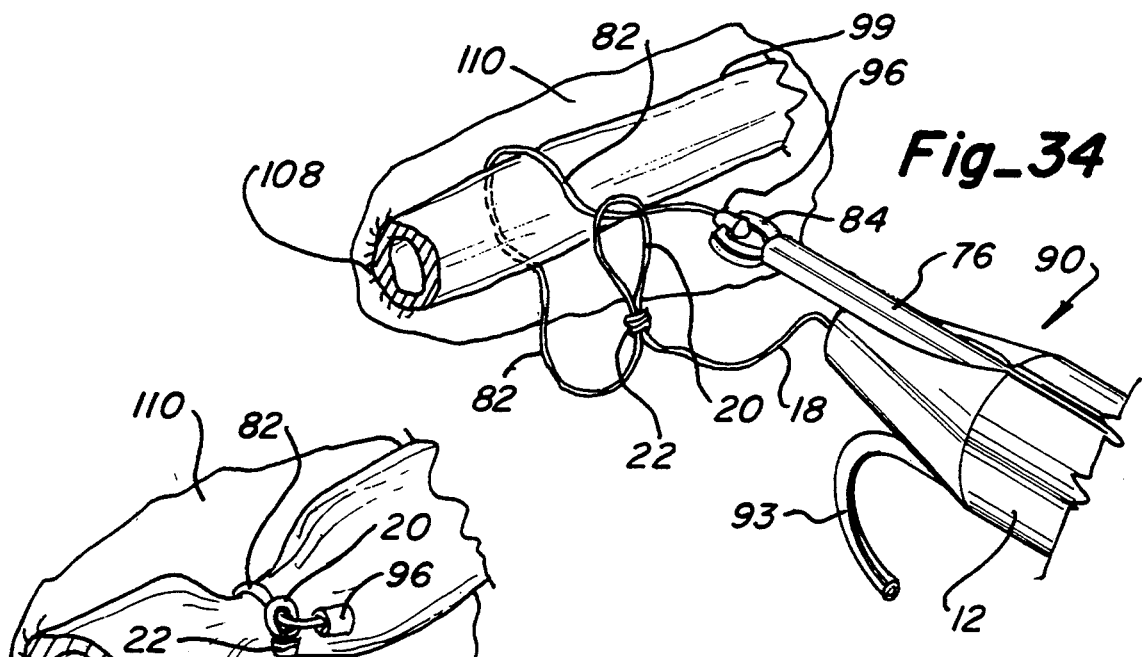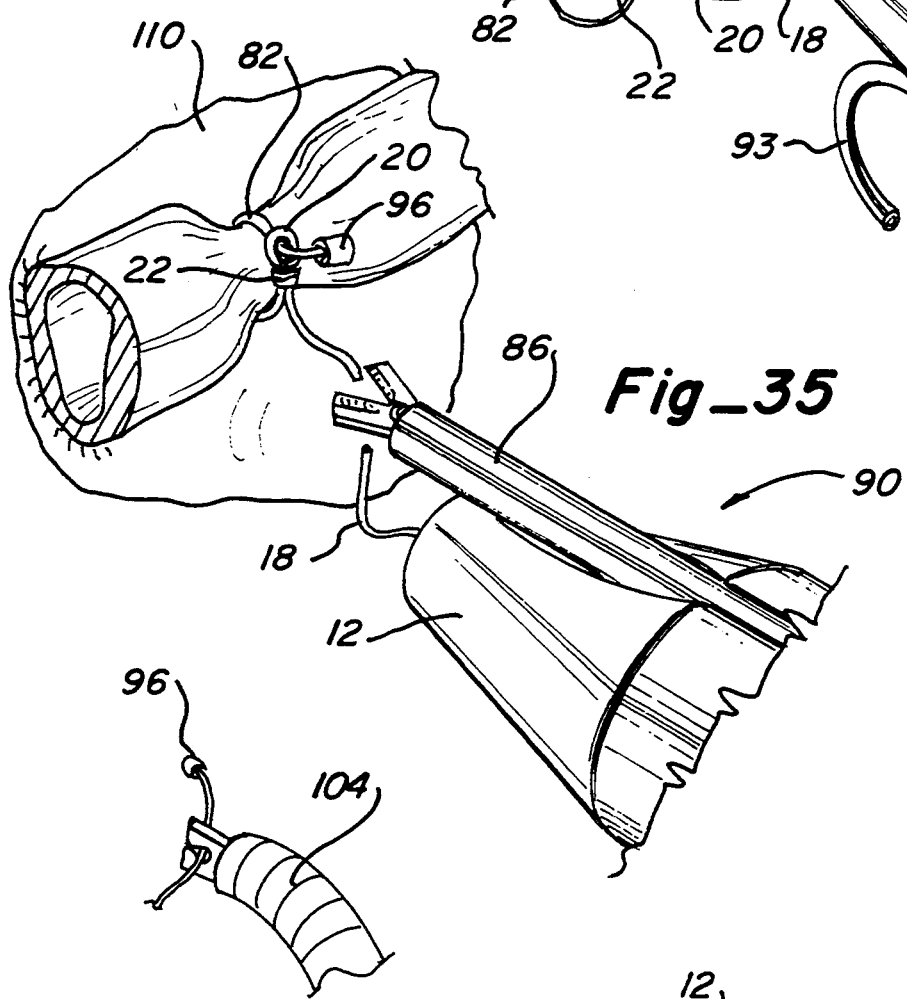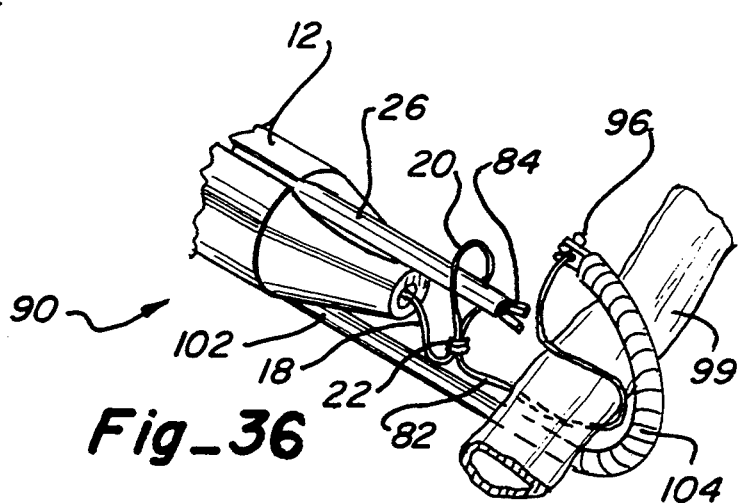

PARALLEL CHANNEL FIXATION, REPAIR AND LIGATION SUTURE DEVICE

TECHNICAL FIELD

This application is a continuation-in-part of my U.S. patent application Ser. No. 07/877,076, filed May 1, 1992.

This invention relates to a laparoscopic surgical ligation devices and particularly ones which provide means for positioning a tissue to be ligated, repairing a tissue, completing a ligation and for coagulation and fulguration of a ligated tissue.

BACKGROUND ART

There are several manufacturers of laparoscopic surgical devices for tubal ligation. These devices generally utilize a hollow plastic tube containing a pre-formed loop of suture material with a slip knot at the terminal end. The other end of the suture terminates in a plastic handle or puller which allows easy application of traction to the device to close the loop around the tissue to be ligated inside the patient's body. A tapered distal end on the plastic tube forces the closure of the slip knot as the surgeon applies pressure to the puller causing strangulation of the tissue within the loop. Once the strangulation is sufficient to satisfy the surgeon utilizing the device, scissors are inserted through another trochar and excess suture material is cut-off adjacent the slip knot.

These devices have proven particularly helpful in endoscopically ligating blood vessels, appendix stumps and similar structures. Suture material used in the devices includes both absorbable suture material such as cat gut and non-absorbable suture materials such as silk. Other proprietary types of suture material have also been used.

The disadvantages of these devices is that at least two additional portals, formed with trochars, are required. One is for viewing via a laparoscope and the third portal is for providing a surgical clamp and/or surgical scissors. The laparoscope is used to visually monitor the procedure being done. A surgical clamp is used to grasp the tissue to be ligated by the suture loop and the scissors are used to cut away excess suture material after the ligation has been completed.

The following patents are exemplary of the prior art:

Komiya, U.S. Pat. No. 4,018,229, shows a rather complex tool for internally attaching a loop and securing it around an affected part in a coeloma.

Shannon et al. U.S. Pat. No. 3,476,114; Mulhollan et al., U.S. Pat. No. 4,602,635, and Ferguson et al., U.S. Pat. No. 3,877,434, each show ligating instruments used to tie a knot to secure the structure being held.

West German Patent No. 2,804,070 and USSR Patent No. 552,077 also show ligature knot tying devices.

Takamatsu, U.S. Pat. No. 4,487,489, shows an endoscope having an electrode loop for clamping a tissue. The endoscope also includes means for viewing the operative site.

Wheeler, U.S. Pat. No. 4,607,621, discloses an endoscopic device utilizing a loop for extending around a body tissue and has an electrode plate upon which the patient rests during the operative procedure for completing an electrical path. The endoscope also has viewing means.

Thus, while the foregoing patents are suitable for their intended purpose, they do not overcome the disadvantages set forth above.

DISCLOSURE OF THE INVENTION

In accordance with this invention, a laparoscopic surgical ligation, repair and electrosurgical coagulation and cutting device is provided. This device has an elongated distally tapered handle sized to be received in a trochar and having a central passageway extending therethrough. A first channel is provided in the handle along one side of the passageway and is generally parallel thereto. A second channel is provided in the handle which is generally parallel to the passageway and spaced from the first channel. A suture extends through the central channel passageway and has a loop with a slip knot on the distal end thereof and a pull on the proximal end thereof, so that by pulling on the pull the loop can be drawn tightly about a tissue to be ligated. An electrosurgical wire is slidably received in the first channel and has an electrically insulated body extending through the first channel with an exposed wire hook formed at the distal end thereof for grasping the tissue to pull it through the suture loop. An electrical connector is attached to the proximal end thereof for connection to a source of electrosurgical power. A ligation assist device is slidably received in the second channel which may be in the form of a hypodermic needle for providing anesthesia to the tissue to be ligated or in the form of an optical fiber for carrying laser energy for fulgurating the ligated tissue.

As will be apparent, the device just described is very versatile. The hook, which extends through the first channel, provides means for manipulating the tissue to be ligated and positioning it within the suture loop, so that the loop can be drawn tightly about the tissue to strangulate it. In addition, a cutting blade can be provided on the hook for cutting the suture close to the knot after the suture has been drawn tight. The hook can be an electrosurgical instrument to be used to coagulate the ligated tissue. Also, the second channel can be used initially by a hypodermic needle so that the tissue to be ligated can be anesthetized prior to ligation, if need be. Also, the same channel can be used subsequentially for an optical fiber for providing laser energy to fulgurate the ligated tissue.

By the use of this device, only two portals are necessary for ligation procedures, the one for this device and a second portal for viewing through an endoscope. Thus, the laparoscopic procedure is simplified and accomplished with less trauma and discomfort to the patient.

Other common surgical procedures are simplified by devices further disclosed as modifications and enhancements of the present invention. For example, fixation sutures are used extensively in surgery to temporarily hold an organ or other body part to a body cavity wall. To simplify the procedure for engaging a fixation suture, in accordance with this disclosure, a laparoscopic fixation suture device is provided. This device has an elongated distally tapered handle having a central passageway, as in the present invention, but only a single first channel is provided. A suture extends through the central passageway and has a suture needle on the distal end thereof and a pull on the proximal end thereof. A nesting tube is slidably received in the first channel and has a distal opening to frictionally receive the suture needle.

A second laparoscopic device provided with forceps can be used to remove the suture needle from the nesting tube and pass it through the organ to be fixed to the body cavity wall. When the needle is replaced in the nesting tube, both ends of the suture can be withdrawn into the device and the device pulled out from the body cavity wall. Thereby the two suture ends may be passed through the body cavity wall and tied over a bolster. Thus, the application of a fixation suture is greatly simplified. The suture may be cut at a later time, allowing the organ to return to its normal position.

Also, in accordance with another form of this invention, a laparoscopic body part repair device is provided to simplify the repairing of structures inside a body cavity. This device also utilities a distally tapered handle, central passageway, and a first channel. A suture extends through the central passageway and has a loop with a slip knot on the distal end thereof and a pull on the proximal end thereof. A portion of the suture extends beyond the slip knot and has a suture needle attached thereto. The needle is frictionally received in the distal tapered end of the first channel. After the defect is repaired by utilizing a laparoscopic forceps device to remove the suture needle and make the stitches, the suture needle is passed through the loop. Then by simultaneously pulling on the pull and the laparoscopic forceps device, the loop is easily closed, thus eliminating tedious and time consuming ligature knotting to complete the suture. The needle may then be reinserted into the channel and the excess suture cut to allow the laparoscopic body part repair device to be removed.

Clip appliers and staplers are not significantly reliable for the ligation of larger and medium sized blood vessels, cystic ducts, trachea and bronchi. In accordance with a further form of this invention, a laparoscopic suture carrying device is provided to simplify the ligation of certain vessels with a high assurance of complete surgical closure. This device utilizes a handle, having a tapered distal end, a central passageway, and a first and second channel. A suture extends through the central passageway and has a loop with a slip knot on the distal end thereof and a pull on the proximal end thereof. A portion of the suture extends beyond the slip knot and has a tab attached thereto. A carrier device is slidably received in the second channel. The carrier device has a generally U-shaped curvature at its distal end with a receiving means for the suture extension and tab. The U-shaped curvature may be deformable. For example, the suture extension and tab can be loaded in the tube through a slit along the inner surface of the curvature. A laparoscopic forceps device is slidably received in the first channel. Once the tab is brought behind the vessel to a ligated, the laparoscopic forceps device is used to draw the tab through the loop. Then the ligation and suture loops are closed by simultaneously pulling on the tab with the forceps and the pull by hand. The carrier device can be a deformable j-guide carrier with a slotted tip to releasably hold the suture tab.

Additional advantages of this invention will become apparent from the description which follows, taken in conjunction with the accompanying drawings.

BRIEF DESCRIPTION OF THE DRAWINGS

FIG. 1 is a perspective view of the laparoscopic surgical ligation and electrosurgical coagulation and cutting device of this invention;

FIG. 2 is an enlarged vertical section, taken along line 2—2 of FIG. 1, showing the internal structure of the handle;

FIG. 3 is an enlarged fragmentary horizontal section, taken along line 3—3 of FIG. 1, showing further details of the distal end of the handle and showing it positioned within a trochar;

FIG. 4 is an end view of FIG. 3, taken along line 4—4 thereof with the trochar omitted;

FIG. 5 is a longitudinal section, similar to FIG. 3, but showing the hook retracted and the trochar omitted;

FIG. 6 is an end view of FIG. 5, showing the hook in retracted position;

FIG. 7 is a section taken along line 7—7 of FIG. 6, showing the recess for receiving the hook;

FIG. 8 is a perspective view of the device showing its use with a hypodermic needle;

FIG. 9 is a perspective view of the device showing its use with a optical fiber for transmitting laser light;

FIG. 10 is a fragmentary perspective view showing the positioning of the suture loop over tissue, such as a tubular portion to be ligated;

FIG. 11 is a fragmentary perspective view, similar to FIG. 10, but showing the hook pulling the tubular tissue to be ligated through the suture loop;

FIG. 12 is a fragmentary perspective, similar to FIGS. 10 and 11, showing the suture loop being drawn around the tubular portion to ligated;

FIG. 13 is a fragmentary perspective view showing the suture loop drawn tight about the tubular portion to be ligated;

FIG. 14 is a fragmentary perspective view showing the knife on the hook being used to cut the suture material adjacent the slip knot;

FIG. 15 is a perspective view of the completed ligation;

FIG. 16 is a fragmentary perspective view showing the hook used as an electrosurgical device for cauterizing and cutting the ligated tissue;

FIG. 17 is a fragmentary perspective view of an optical fiber supplying laser light to fulgurate the ligated tissue;

FIG. 18 is a perspective view of another embodiment of this invention comprising a laparoscopic fixation suture device;

FIG. 19 is an enlarged fragmentary vertical section, taken along line 19—19 of FIG. 18, showing the distal end of the tapered handle and the needle in a nesting tube;

FIG. 20 is a fragmentary perspective view showing the needle being removed from the nesting tube with a laparoscopic forceps device introduced through a second trochar;

FIG. 21 is a fragmentary perspective view showing the needle being passed through a body part while being observed through an endoscope;

FIG. 22 is a fragmentary perspective view showing the two suture ends being passed through the body cavity wall;

FIG. 23 is a fragmentary perspective view showing the suture being tied around the bolster fixing the organ to the body cavity wall;

FIG. 24 is a fragmentary perspective view of a further embodiment of this invention comprising the laparoscopic body part repair device of this invention;

FIG. 25 is a fragmentary perspective view showing the body part being repaired and the needle being drawn through the suture loop;

FIG. 26 is a fragmentary perspective view showing the suture loop being drawn and tightened;

FIG. 27 is a fragmentary perspective view showing the suture ends being cut adjacent to the knot;

FIG. 28 is a fragmentary perspective view of an additional embodiment of this invention comprising a laparoscopic suture carrying device of this invention;

FIG. 29 is a fragmentary perspective view showing the suture loaded in the carrier device;

FIG. 30 is a horizontal section, taken along line 30—30 of FIG. 29, showing the suture loaded in the carrier device;

FIG. 31 is a fragmentary perspective view showing the suture being placed behind the vessel to be ligated;

FIG. 32 is a sectional view, taken along line 32—32 of FIG. 31, showing the placement of the suture behind the vessel to be ligated;

FIG. 33 is an enlarged, fragmentary, side view showing the suture tab being grabbed by the laparoscopic forceps device in the second channel;

FIG. 34 is a fragmentary perspective view showing the suture tab being drawn through the loop FIG. 35 is a fragmentary perspective view showing the suture ends being cut adjacent to the knot;

FIG. 36 is a fragmentary perspective view of a laparoscopic suture carrying device with slotted tip of this invention showing the suture being released from the slotted tip and drawn through the loop; and FIG. 37 is a fragmentary, enlarged, perspective view showing the slotted tip.

BEST MODE FOR CARRYING OUT THE INVENTION

In accordance with this invention, a laparoscopic surgical ligation, repair, and electrosurgical coagulation and cutting device 10 is provided. This device is designed primarily for female sterilization in an out patient and/or office setting under local anesthesia. However, it can also be used for ligating blood vessels, for laparoscopic appendectomies or for any other tissue ligation procedure. This device can be introduced through the abdomen to the operative site by means of a 3 mm or 5 mm trochar opening. Viewing is done through an endoscope such as the electronic endoscope shown in my U.S. Pat. No. 5,188,094 entitled "Heat Sterilizable Electronic Video Endoscope", which is introduced through a separate trochar. Since this optical catheter is a microendoscope, it can also be introduced through a 3 mm opening under local anesthesia. This, however, does not preclude the use of a much larger laparoscope, still utilizing local anesthesia.

Laparoscopic device 10 comprises an elongated body or handle 12, which may be extruded from a medically compatible plastic or other suitable material. The device can be introduced through a trochar of an endoscope, such as trochar 14, shown in FIG. 3. A suitable device is shown in my U.S. Pat. No. 4,869,717, for "Gas Insufflation Needle With Instrument Port".

Handle 12 has a central suture passageway 16 through which a suture or suture line 18 extends. The distal end of suture 18 is formed with a loop 20 by means of a slip knot 22. The slip knot has a diameter larger than that of passageway 16. The proximal end of suture 18 has a suture line pull in a form of a handle 24.

A first channel 26 runs entirely along and intersects the surface of handle 12 to form a longitudinal groove which is generally parallel to passageway 16. This channel slidably receives an electrosurgical wire 28 which is covered by electrical insulation 30 and terminates at the distal end in an exposed wire hook 32. A cutting blade 34 can be provided across the bight of the hook, as best seen in FIG. 3. The proximal end of wire 28 is connected to an electrical connector 36 for attachment to a source of electrosurgical power (not shown). Wire 28 is longitudinally slidable and rotatable within channel 26 so that the tip of hook 32 can be used to grasp the tissue to be ligated and draw it through loop 20, as will be described more fully below. The cutting blade 34 can be used to cut the suture just beyond slip knot 22 after the loop is drawn tight, as further explained below. Conveniently, when not in use, wire 28 can be drawn in the proximal direction so that the hook 32 and blade 34 are received in a recess 38 formed in the distal end of handle 12 as a transverse slot across the convex end of handle 12 and intersecting the end of channel 26, as best seen in FIGS. 3–7.

An optional second channel 40 can be provided which also runs the entire length of handle 12, but spaced from channel 26, such as on the opposite side of passageway 16 from channel 26. This second channel 40 intersects the surface of handle 12 to form a longitudinal groove which is also generally parallel to passageway 16. Channel 40 can be used selectively for receiving other ligation devices. For example, in FIG. 8, a hypodermic syringe 42 is shown with a long needle 44 attached thereto which extends through channel 40. It can be used initially to inject anesthesia to the tissue to be ligated, if this procedure is deemed necessary. Usually, the anesthesia used to deaden the area of the abdomen where the trochars are inserted is sufficient and additional anesthesia is not required.

Alternatively, channel 40 can be used to receive one or more optical fibers, such as optical fiber 46. Conveniently, the optical fiber can be connected to a suitable source 48 of laser light, as shown in FIG. 9, for providing laser light to the operative site to fulgurate the ligated tissue.

The method of preforming a tubal ligation is diagrammatically illustrated in FIGS. 10–17. In FIG. 10, tissue to be ligated, such as fallopian tube 50 is shown. The device 10 is positioned so that suture loop 20 is brought into proximity to a tubal section 52 of the tube 50 which is to be ligated. As previously mentioned, this positioning is viewed through an endoscope inserted through a separate trochar. Once loop 20 is positioned, hook 32 is extended to grasp the tubal section 52 and pull it through suture loop 20 as shown in FIG. 11. The physician then pulls on handle 22 to place suture 18 under traction so that loop 20 begins to pull tight around tubal section 52, as shown in FIG. 12. Thus, slip knot 22 engages the distal end of handle 12 and is held by it as the suture is drawn through knot 22 to draw loop 20 tightly about tubal section 52. Hook 32 then is retracted, as shown in FIG. 13, as the final tightening of the slip knot is completed.

Once suture loop 20 has been pulled tight, the hook 32 can be extended again so that blade 34 can be used to cut suture 18 just above slip knot 22, as shown in FIG. 14. The completed ligation is shown in FIG. 15.

For many physicians, this constitutes the end of the procedure. However, other physicians may choose to use the hook 32 as an electrosurgical device for cauterizing the ligated portion 52. This device may be used as either a mono-polar or a bi-polar unit. As illustrated in FIG. 16, the wire hook is positioned adjacent ligated tissue 52 and electrosurgical current is supplied to the hook to carry out the cauterizing procedure.

If desired, an additional or alternative procedure may be undertaken wherein the laser fiber 46 is used for photo coagulation of ligated section 52 or for photo vaporization of the tissue, as illustrated in FIG. 17.

Other common surgical procedures are simplified by devices further disclosed as modifications and enhancements of the present invention. For example, fixation sutures are used extensively in surgery to hold an organ, temporarily, to a body cavity wall. In the abdominal cavity, fixation sutures are used to temporarily hold organs such as the stomach, large bowel, small bowel and gall bladder to the abdominal wall. In accordance with this disclosure, a laparoscopic fixation suture device 70 is provided. This device has an elongated handle 12, shown with a tapered distal end, having a central passageway 16, as in the present invention, but only a single first channel 26 is utilized. A suture 18 extends through said central passageway and has a rigid and generally straight suture needle 72 on the distal end thereof and a pull 24 on the proximal end thereof. A nesting tube 74 is slidably received in the first channel 26 and has a distal opening to frictionally receive the suture needle 72. The nesting tube 74 may be made of medically compatible plastic, stainless steel, or other suitable material.

A second laparoscopic device provided with forceps 76 can be used to remove the suture needle from the nesting tube 74 and pass it through the organ 77 to be fixed to the body cavity wall 75. When the needle 72 is replaced in the nesting tube 74, both ends of the suture 18 can be withdrawn into the device 70 and the device pulled out from the body cavity wall 75. Thereby the two suture ends may be passed through the body cavity wall 75 and tied over a bolster 78. Thus, the application of a fixation suture is greatly simplified. The suture may be cut at a later time, allowing the organ to return to its normal position. The procedure may be viewed by an endoscope 79.

The method of fixing an organ to a body cavity wall is diagrammatically illustrated in FIGS. 18-23. FIG. 18 shows the laparoscopic fixation suture device 70 with needle 72 nested in tube 74. The needle 72 is frictionally received in tube 74 as shown in FIG. 19. FIG. 20 shows the introduction of laparoscopic fixation device 70 through a first trochar and a laparoscopic device provided with forceps 76 through a second trochar. As seen in FIGS. 20 and 21, the second laparoscopic device 76 is used to remove the needle 72 and pass the suture 18 through the organ 77. FIG. 21 shows the procedure being viewed through endoscope 79 inserted through a separate trochar. FIG. 22 shows the two ends of suture 18 being drawn through the body cavity wall 75 after needle 72 has been replaced in nesting tube 74. The suture 18 ends are then tied over bolster 78 to hold the organ in place as shown in FIG. 23.

Frequently, organs in the abdominal, peritoneum or chest cavities are torn and require sewing of double, triple or more stitches. Doctors frequently have trouble learning and executing the tedious and time consuming procedure of ligature knotting through a laparoscope. Therefore, in accordance with this disclosure, a laparoscopic body part repair device 80 is provided to simplify the repair of structures inside a body cavity. This device, as shown in FIG. 24, also utilities a handle 12, central passageway 16, and a first channel 26. The handle 12 is shown as tapered on its distal end to provide an oblique surface to frictionally fit a needle 72 into first channel 26. It is understood that the distal end shape of handle 12 may be varied and still accomplish this purpose. A suture 18 extends through the central passageway 16 and has a loop 20 with a slip knot 22 on the distal end thereof and a pull 24 on the proximal end thereof. A distal end portion 82 of the suture 18 extends beyond the slip knot 22 and has the suture needle 72 attached thereto. The method of repairing structures in a body cavity is shown in FIGS. 24-27. Originally, the needle 72 is frictionally nested in first channel 26. The defect is repaired by utilizing a laparoscopic forceps device 76 introduced through a second trochar (shown in FIGS. 24-27) to remove the suture needle 72 from first channel 26 and make the stitches. The laparoscopic forceps device 76 is then utilized to pass the suture needle 72 through the loop 20. By simultaneously pulling pull 24 while holding tension on needle 72 with forceps device 76, the loop is easily closed, thus completing the suture. The needle 72 may then be replaced in first channel 26. As shown in FIG. 27, the laparoscopic forceps device 76 can be replaced with a laparoscopic cutting device 86 to cut suture 18 and portion 82 just beyond knot 22, and allow the removal of needle 72 and device 80.

For the ligation of larger and medium sized blood vessels, cystic ducts, trachea and bronchi, clip appliers and staplers are not always reliable. Therefore, ligating must be used to adequately close off the vessel. However, often the surgeon has to first free the vessel from a body part attached to it with fibrous tissue by blunt dissection with a dissecting instrument. Typically, this has to be done to free a space for three ligatures. A device which can carry a ligature behind a vessel greatly simplifies this procedure. Therefore, in accordance with this disclosure, a laparoscopic suture carrying device 90 is provided to facilitate the ligation of certain vessels with a high assurance of complete surgical closure. As shown in FIGS. 28 and 29, this device utilizes a handle 12, shown with a tapered distal end, central passageway 16, first channel 26, and second channel 40. A suture 18 extends through the central passageway 16 and has a loop 20 with a slip knot 22 on the distal end thereof and a pull 24 on the proximal end thereof. A portion 82 of the suture 18 extends beyond the slip knot 22 and has a suture line tab 96 attached thereto. A carrier device 92 is slidably received in the second channel 40. The carrier device 92 has a generally U-shaped curved portion 93 at its distal end with a slit 94 along the inner surface thereof, as shown. As seen in FIGS. 29 and 30, the suture end 82 with the tab 96 can be loaded in the carrier device 92 through the slit 94. The carrier device 92 can be made of pre-formed plastic, having a memory, such that the curvature 93 can be straightened when retracted into second channel 40. As shown in FIG. 33, a laparoscopic forceps device 76 is slidably received in the first channel 26.

The method of ligation for major vessels or ducts is shown in FIGS. 31-35. The suture end 82 and tab 96 are brought behind the vessel 99 to a ligated by tilting device 90 and then straightening it. This sufficiently pierces fibrous tissue 108 connecting vessel 99 to body part 110 to allow for the through placement of curved portion 93 of carrier device 92. The laparoscopic forceps device 76 in first channel 26 is used then to draw the tab 96 through the loop 20. The device 90 can again be tilted to withdrawn carrier device 92 from behind vessel 99 and swing it out of the way. Then the ligation 92 and suture 20 loops are closed by simultaneously pulling on the tab 96 with the forceps 84 and the pull 24 by hand. As shown in FIG. 35, once the ligature is closed, the forceps device 76 can be replaced with a laparoscopic scissors device 86 to cut the excess suture beyond the knot 22.

As seen in FIGS. 36 and 37, the carrier device 92 may be replaced by a j-guide carrier 104 with a slotted tip 106 to releasably hold the suture tab 96. The j-guide carrier 104 may either be of pre-formed plastic or may be hollow with a guide wire running through it such that the memory of the plastic forms the curvature when the guide wire is removed.

From the foregoing, the advantages of this invention are readily apparent. A laparoscopical surgical ligation, repair, and electrosurgical coagulation and cutting device has been provided which is simple in construction, yet versatile in use. It can be used for ligating tissue and provides a ready means for cutting the suture once a slip knot has been drawn tight around the tissue to be ligated. The hook has three uses: (1) to position the tissue to be ligated, (2) to use a blade connected thereto for cutting the suture material after ligation and (3) to serve as an electrosurgical device to cauterize the ligated tissue. In addition, the handle has a channel for initially, slidably receiving a hypodermic needle for anesthetizing the tissue to be ligated and subsequently for slidably receiving a laser fiber for coagulation or photo vaporization of the ligated tissue.

Additional advantages of various adaptations of the present invention are also readily apparent. One adaptation of the device, utilizing a nesting tube provided in one of the channels to receive a suture needle attached to a loopless suture, provides for body part to be more easily sutured to a body cavity wall. Another adaptation, utilizing a tapered handle to frictionally receive suture needle attached to a looped and slip knotted suture, provides for a tear or rupture in a body part to be repaired by suturing through one or more laparoscopies without the necessity of tying ligature knots inside the body cavity. A third adaptation, utilizing a curved carrying device in one channel and a ligation assist device in the other channel, provides for ligation of large vessels, often attached to a body part by fibrous tissue, to be accomplished in a much more facile manner.

This invention has been described in detail with reference to particular embodiments thereof, but it will be understood that various other modifications can be effected within the spirit and scope of this invention.

I claim:

1. A laparoscopic fixation, repair and ligation suture device adapted for multi-stitch repairing of an organ inside a body comprising:

an elongated handle having a distal end, a proximal end, a central suture receiving passageway extending along the entire length of said handle and having a diameter slightly larger than a diameter of a suture line, and a first channel extending along the entire length of said handle on one side of said passageway, generally parallel to said central passageway for frictionally receiving and storing a point end of a rigid and generally straight suture needle;

a suture line extending through the entire length of said central passageway having a length greater than the length of said handle, a proximal end of said suture line extending beyond the proximal end of said handle and having a suture line pull attached thereto, said suture line pull having a diameter greater than the diameter of said central passageway, a distal end of said suture line extending beyond the distal end of said handle and having a rigid and generally straight suture needle attached thereto; and a loop with a slip knot formed on said suture line at a point distally spaced from the distal end of said handle, said slip knot having a diameter larger than the diameter of said central passageway to prevent said loop from entering said passageway, a distal portion of said suture line distally extending beyond said slip knot.

2. A laparoscopic fixation, repair and ligation suture device adapted for fixing an organ to the inside of a body cavity wall comprising:

an elongated handle having a first length, a distal end, a proximal end, a central suture receiving passageway extending along the entire length of said handle and having a first diameter slightly larger than a diameter of a suture line, a first channel extending along the entire length of said handle on one side of said passageway, generally parallel to said central passageway for slidably receiving a nesting tube therein;

a suture line extending through the entire length of said passageway and having a length greater than at least twice the length of said handle, a proximal end of said suture line extending beyond the proximal end of said handle and having a suture line pull attached thereto, said suture line pull having a diameter greater than the diameter of said central passageway, a distal end of said suture line extending beyond the distal end of said handle and having a rigid and generally straight suture needle attached thereto, said needle having a diameter; and a nesting tube slidably received in said first channel and having a length greater than the length of said handle so that said nesting tube is extendable beyond said distal end of said handle, said nesting tube having an internal diameter generally equal to the diameter of said rigid needle, said nesting tube further having an opening at the distal end thereof for frictionally grasping said rigid needle when said needle is inserted therein through said distal end opening, said nesting tube further having a pull on a proximal end thereof so that by pulling in a proximal direction end thereof so that by pulling in a proximal direction on said nesting tube pull when said rigid needle is grasped inside the distal end of said tube, said rigid needle can be drawn through said first channel and out the proximal end of said handle so that a portion of said suture line adjacent to said needle may be grasped outside the body.

3. A laparoscopic fixation, repair and ligation suture device adapted to ligate vessels and ducts comprising:

an elongated handle having a first length, a distal end, a proximal end, a central suture receiving passageway extending along the entire length of said handle and having a diameter slightly larger than a diameter of a suture line, a first channel for slidably receiving a ligation assist device, said first channel extending along the entire length of said handle on one side of said passageway, generally parallel to said central passageway, said handle further having a second channel for slidably receiving a carrier device, said second channel extending along the entire length of said handle, generally parallel to said central passageway and spaced oppositely from said first channel;

a suture line extending entirely through said central passageway and having a length greater than the length of said handle, a proximal end of said suture line extending beyond the proximal end of said handle and having a suture line pull attached thereto, said suture line pull having a diameter greater than the diameter of said central passageway, a distal end of said suture line extending beyond the distal end of said handle and having a suture line tab attached thereto, said suture line tab having a diameter greater than the diameter of said carrier device;

a loop with a slip knot formed on said suture line at a point distally spaced from the distal end of said handle, said slip know having a diameter larger than the diameter of said central passageway to prevent said loop from entering said passageway, a distal portion of said suture line distally extending beyond said slip knot;

a ligation assist device slidably received in said first channel, said ligation assist device having a length greater than the length of said handle, a distal end of said ligation assist device extendable beyond the distal end of said handle and having means for grasping said suture line tab; and a carrier device slidably received in said second channel, said carrier device having a length greater than the length of said handle, a distal end of said carrier device extendable beyond the distal end of said handle, and forming a curved generally U-shaped portion said curved U-shaped portion having a distal end, a curvature diameter equal to the spacing between said first and second channels, and receiving means to receive said distal portion of said suture line such that, when said suture line distal extension portion is held by said receiving means, said suture line tab is axially aligned with said first channel and capable of being directly grasped by said grasping means of said ligation assist device when said ligation assist device is distally extended through said first channel.

4. A laparoscopic device, as claimed in claim 3, wherein:

said U-shaped portion is made from a hollow tube having a diameter greater than the diameter of said suture line and less than the diameter of said tab; and said receiving means includes a slit along said curved U-shaped portion through which said suture line distal extension portion may be loaded into said hollow tube with said suture line tab held adjacent to the distal end of said U-shaped portion.

5. A laparoscopic device, as claimed in claim 3, wherein:

said receiving means includes a slotted tip extending from the distal end of said U-shaped portion to releasably receive said suture line extension portion with said suture line tab held adjacent to said slotted tip.

6. A laparoscopic device, as claimed in claim 3, wherein:

said U-shaped portion of said carrier device is deformable to a generally straight configuration when said U-shaped portion is in a retracted position within said second channel.

* * * * *